United States Patent [19]

Eichenhofer et al.

[11] 4,005,179

[45] Jan. 25, 1977

[54] WORKING UP SYNTHESIS SOLUTIONS OBTAINED IN PRODUCTION OF HYDRAZINE

[75] Inventors: Kurt-Wilhelm Eichenhofer, Leverkusen; Reinhard Schliebs, Cologne, both of Germany; Hermann Brandl, Baytown, Tex.; Heinrich Kohnen, Leverkusen-Schlebusch, Germany

[73] Assignee: Bayer Aktiengesellschaft, Leverkusen, Germany

[22] Filed: July 18, 1975

[21] Appl. No.: 597,263

[30] Foreign Application Priority Data

July 27, 1974 Germany .................. 2436335

[52] U.S. Cl. .................. 423/407; 423/408; 260/566 B
[51] Int. Cl.² .................. C01B 21/16
[58] Field of Search .................. 423/407, 408; 260/566 B

[56] References Cited

UNITED STATES PATENTS

| | | | |
|---|---|---|---|
| 2,830,050 | 4/1958 | Biel .................. | 260/566 B |
| 3,063,806 | 11/1962 | Heinrich et al. .................. | 423/407 |
| 3,869,541 | 3/1975 | Weiss et al. .................. | 423/407 |
| 3,875,231 | 4/1975 | Brandl .................. | 260/566 B |

FOREIGN PATENTS OR APPLICATIONS

| | | | |
|---|---|---|---|
| 2,010,123 | 9/1970 | Germany .................. | 260/566 B |
| 1,137,505 | 12/1968 | United Kingdom .................. | 260/566 B |

OTHER PUBLICATIONS

Audrieth, L. F. et al., *The Chemistry of Hydrazine,* John Wiley & Sons, 1951, N.Y. p. 45.

*Primary Examiner*—G. O. Peters
*Attorney, Agent, or Firm*—Burgess, Dinklage & Sprung

[57] ABSTRACT

In the production of hydrazine wherein aqueous ammonia is oxidized in the presence of a ketone to form an aqueous solution containing at least one of a hydrazone and a ketazine along with ammonia, the hydrazone and ketazine are concentrated and the hydrazone and ketazine are subsequently hydrolyzed to hydrazine and ketone, the improvement which comprises effecting the concentration of the hydrazone and ketazine by extracting the aqueous solution with a substantially water-immiscible organic solvent whereby the hydrazone and ketazine preferentially enter the water-immiscible solvent, and separating the water-immiscible solvent extract from the aqueous solution. The organic solvent is preferably a higher alcohol, a chlorinated hydrocarbon, benzene or a substitution product thereof. The organic solvent extract, in one or more stages, and optionally with addition of ketone, can be re-extracted with water, hydrolyzed with aqueous acid or subjected to distillation to separate the hydrazine values from the organic solvent.

24 Claims, 2 Drawing Figures

WORKING UP SYNTHESIS SOLUTIONS OBTAINED IN PRODUCTION OF HYDRAZINE

The present invention relates to a process for working up the hydrazine values from synthesis solutions obtained in its production.

Basically, there are three processes for the production of hydrazine. In the classical "Raschig process", sodium hypochlorite and ammonia or chloramine and ammonia are reacted to form hydrazine and sodium chloride (U.S. Pat. Specifications Nos. 910,858, 2,863,728 and 2,715,061). In the "ketone process", hydrazine is synthesized from sodium hypochlorite and ammonia in the presence of ketone or ketone/ammonium salts. Hydrazones and ketazines or 3,3-diorganyl diaziridines are formed as intermediate products and can be converted into the ketazines with catalytic quantities of acid (German Patent Specifications Nos. 1,082,889, 1,088,939, 1,103,903 and 1,126,395 and German Offenlegungsschrift No. 1,695,585). It is also known that ketazines can be obtained from hydrogen peroxide, ammonia and ketones in the presence of nitriles, esters, imides and amides, which are converted into amides or ammonium salts of the corresponding acids, or from organic and inorganic peracids, ammonia and ketone (German Offenlegungsschrifts Nos. 2,127,229, 2,143,516, 2,210,790 and 2,314,038). Whereas the synthesis can be carried out with very high yields of, in some cases, more than 90% using simple technical means, problems are involved in working up these synthesis solutions, i.e. in separating the reaction products hydrazine, hydrazone and ketazine. The problems involved in separation are attributable to the low concentrations of the required products hydrazine, hydrazone and ketazine in the reaction mixture, and to the high content of inorganic salts or organic reactants.

It is known that hydrazine-containing solutions of the type formed in the Raschig process can be worked up by concentrating them by evaporation until the hydrazine-water azeotrope passes over. The high specific energy consumption and the heavy losses of hydrazine occasionally encountered during concentration by evaporation, and also the fact that sodium chloride is precipitated during this process and considerably inhibits evaporation, do not offset the advantage that the hydrazine is directly obtained. Even the further development of this working up process has not eliminated the high specific energy consumption (U.S. Patent Specification Nos. 2,917,369 and 2,799,631).

It has also been proposed to extract hydrazine from hydrazine-containing solutions by using certain fluoralcohols (U.S. Patent Specification No. 3,321,284). Apart from the fact that the fluoralcohols used are difficult to obtain on a commercial scale, but above all are expensive, this process suffers from poor distribution coefficients.

It has also been proposed to work up hydrazine-containing solutions with acetone and higher ketones by distillation following conversion of the hydrazine into the ketazine (German Patent Specification No. 1,048,884). Shifting of the addition of acetone during the synthesis resulted in the ketone processes, in all of which the ketazines formed are separated off by distillation using their water azeotropes (German Patent Specification No. 1,273,503). In this respect, a distinction has to be drawn between processes based on dimethyl ketazine and processes based on higher ketazines.

It is known that higher ketazines whose parent ketone contains more than 3 carbon atoms can be distilled off from the reaction mixture relatively easily by virtue of minimal azeotrope formation with water (British Patent Specification No. 1,174,234, German Patent Specification No. 1,282,617, British Patent Specification No. 1,174,235), or that they can be separated off by the addition of hydrophilic substances, more especially salts, for example sodium chloride, in which case the system is split into two phases and the phase containing the reaction products of hydrazine with ketones is separated off from the aqueous phase (German Offenlegungsschrift No. 2,056,357). This advantage of higher ketazines, i.e. the fact that they can be separated off relatively easily, is offset both by the higher price of higher ketones, compared with acetone, and also by the greater outlay in terms of equipment and energy consumption which subsequent hydrolysis into hydrazine and ketone involves by comparison with dimethyl ketazine. In all working-up processes involving additions of salts or other hydrophilic substances, the accumulated salt ballast increases to an undesired extent.

It is known that aqueous solutions of dimethyl ketazine produced by known processes can be worked up into ketazine by distilling the dimethyl ketazine/water azeotrope following the removal of ammonia (German Patent Specification No. 1,273,503). The disadvantage of this process is that, when the ammonia is removed, the dimethyl ketazine formed in the synthesis stage is partly hydrolyzed into dimethyl hydrazone and, in some cases, even further into hydrazine, so that the dimethyl hydrazone formed has to be converted back into the dimethyl ketazine by the addition of acetone before removal by distillation in the form of the ketazine-water azeotrope. In addition, the dimethyl ketazine undergoes hydrolysis again during azeotropic distillation, with the result that distillation has to be carried out with vigorous recycling of acetone and in the presence of excess acetone. This working up process is also expensive on account of its high specific energy consumption.

Another known process for the production of hydrazine comprises a liquid-liquid extraction as part of a hydrolysis process using an alkali as the hydrolyzing agent (German Offenlegungsschrift No. 1,965,898). In this process, the solvents toluene and benzene are said to be used during working up for removing the acetone formed by hydrolysis from diaziridine or hydrazone-acetone solutions in the presence of aqueous alkali, the aqueous alkali phase being said to contain free hydrazine. This process cannot be used for working up synthesis solutions because the diaziridines and hydrazones used cannot be split up with alkalis into ketone and hydrazine, and because hydrazones can only be split into ketazine and hydrazine by disproportionation. The presence of salt and excess ammonia or other components in addition to the low concentrations of hydrazine or hydrazone or ketazine present in the synthesis solutions, also make this process unsuitable for working up. British Patent Specification No. 1,191,630 describes the production of hydrazine from pure aqueous ketazines and hydrazone solutions by a process based on the extractive disproportionation of hydrazone. Hydrocarbons, chlorinated hydrocarbons, alcohols with more than 4 carbon atoms and cyclohexanol are mentioned as extractants. These extractants are added in order to extract from the equilibrium mixture the ketazine formed in addition to hydrazine during the disproportionation of hydrazone, and at the same time to produce an aqueous hydrazine solution which still contains hydrazone. The yields of free hydrazine obtained in this process only amount to around 60%.

The object of the present invention is to find a more effective method than the minimum ketazine-water azeotrope method for working up aqueous synthesis solutions in the production of hydrazine which can be applied to the synthesis solutions accumulating in the various known processes and which can be carried out with simple means.

Accordingly, the present invention relates to a process for working up aqueous synthesis solutions in the production of hydrazine, containing hydrazones and/or ketazines, optionally ketones and other organic and/or inorganic compounds emanating from the production of the aqueous synthesis solutions, distinguished by the fact that the hydrazone and/or ketazines and, optionally, the ketones of the synthesis solutions are extracted with water-immiscible organic solvents; ammonia and/or other readily volatile compounds are removed from the extract; and the hydrazones and/or ketazines are subsequently separated off from the water-immiscible solvents and converted into hydrazine hydrate or hydrazinium salts and ketone by treatment with water and/or acids, optionally under pressure.

The water-immiscible or substantially water-immiscible organic solvents preferably used for the purposes of the invention are chlorinated hydrocarbons with from 1 to 3 carbon atoms and from 1 to 5 chlorine atoms, benzene, substituted benzenes and alcohols with from 5 to 18 carbon atoms.

Examples of chlorinated hydrocarbons are dichloromethane, trichloromethane, tetrachloromethane, dichloroethane, trichloroethane, trichloroethylene and pentachloropropane. Trichloromethane, dichloromethane and dichloroethane are preferably used.

Examples of benzene substituents are amino, halo, cyano, nitro, lower alkyl, lower alkoxy and carbo-lower alkoxy, "lower" having reference to 1 to about 4 carbon atoms, e.g. aniline, 4-benzonitrile, toluene, nitrobenzene, 2-chloraniline, 3-chloraniline, 1,2-dichlorobenzene, 2-nitrotoluene, 2-methoxyaniline, 2-carbomethoxy-aniline and 1-chloro-2-methyl-3-aminobenzene. 3-Chloraniline and 2-chloraniline are preferably used.

In one particularly preferred embodiment of the process according to the invention, extraction is carried out with at least one higher alcohol, e.g. hydroxy-substituted hydrocarbons including aliphatic and cycloaliphatic alkanols containing at least 5 carbon atoms. Examples of suitable higher alcohols are n-pentanol, n-hexanol, cyclohexanol, n-heptanol, n-octanol, n-nonanol, n-dodecanol, 2-ethyl-hexanol, 2-ethylbutanol, 3,5,5-trimethyl-heptanol, 3,5-dimethyl-hexanol, i-tridecanol, i-octadecanol, 4-ethyl-octanol or alcohol mixtures, each of the components of the mixture containing at least 5 carbon atoms, for example $C_7$ and $C_8$ or $C_7 - C_9$ cuts from oxo synthesis. The type of alcohol used, i.e. whether the alcohol is cyclic, branched or linear, has only a minimal bearing upon the workability of the process. It is particularly preferred to use higher alcohols ROH or alcohol mixtures which boil at temperatures above about 150° C under normal pressure, have a solubility in water equivalent to less than about 0.1% by weight, are able to dissolve less than about 4% by weight of water and whose azeotrope with water boils at a temperature above 99° C, the azeotrope containing less than about 25% of the alcohol, for example 3-methyl-hexanol, 5-methyl-hexanol, 2-ethyl-hexanol, n-octanol, 3,5,5-trimethyl-hexanol, dimethyl-hexanols, 4-ethyl-octanol, tridecanol, i-tridecanols and i-octadecanols.

Basically, both higher and lower ketones, hydrazones and ketazines (hereinafter also referred to as "organonitrogen compounds"), which correspond to the following general formulae (I), (II) and (III), are suitable for working up by extraction in accordance with the invention on the basis of the following process stages for the production of hydrazine.

In the formulae (I), (II) and (III), $R_1$ and $R_2$ independently of one another can represent linear or branched alkyl, cycloalkyl or aralkyl radicals with from 1 to about 12 carbon atoms, or one of the radicals $R_1$ or $R_2$ may be an aryl radical with up to about 10 carbon atoms, or the radicals $R_1$ and $R_2$ together may complete a cyclic ring system with from 5 to 10 carbon atoms.

Lower ketones with from 3 to 6 carbon atoms are particularly suitable, bearing in mind the economy of the process. Examples of lower ketones of this kind are acetone, 2-butanone, 2-pentanone, 3-pentanone, methyl isopropyl ketone, methyl benzylketone, methyl phenyl ketone, cyclopentanone, cyclohexanone and cycloheptanone. It is particularly preferred to use acetone.

The extractants used in the process according to the invention are able to extract ketazines and hydrazones almost quantitatively and to prevent the formation of hydrazine during extraction, which prevention can be promoted by adding excess ketone.

By virtue of the process according to the invention, it is possible to work up synthesis solutions in the production of hydrazine and to isolate ketazines and/or hydrazones in the form of pure aqueous solutions which may be converted into hydrazine or its salts or into other compounds of hydrazine.

In the context of the invention, synthesis solutions in the production of hydrazine are the reaction mixtures which accumulate in conventional processes following the synthesis of hydrazine, hydrazones and ketazines for the purposes of producing hydrazines or hydrazine compounds by the oxidation of ammonia, which may also be present in bound form, with active halogen or percompounds of any kind in the presence of other components. The synthesis solutions differ in composition according to the way in which the process is carried out. In addition to hydrazine, reaction products of hydrazine with the ketones, hydrazones and ketazines (the molar sum of $N_2H_4$, hydrazone and ketazine is hereinafter referred to as total hydrazine) and water, the following components may be present in the reaction mixture of the synthesis solution: ammonia, ketones, salt-like compounds, alcohols with from 1 to 4 carbon atoms, the extractants according to the invention and other organic components which are required for carrying out the reaction.

The homogeneity of the synthesis solution is not critical to the workability of the process according to the invention. It is possible to work up homogeneous solutions, mixtures with an organic and an aqueous phase, mixtures with an organic and an aqueous phase and a solid phase or mixtures with an aqueous phase and a solid phase. However, it is preferred to work up homogeneous synthesis solutions or mixtures with an organic phase and an aqueous phase without any solid phase.

In cases where the synthesis solution contains free hydrazine, the free hydrazine is converted with ketone into hydrazones or ketazines or mixtures thereof before the extraction stage according to the invention.

The concentration of hydrazine or hydrazone or ketazine or their total concentration in the homogeneous solution, or in the aqueous phase in the case of two-phase solutions, may be between about 0.01 and 5 moles/liter. The preferred concentration range is about 0.01 to 4 moles/liter and more especially about 0.05 to 3 moles/liter.

The solutions may contain ammonia. The concentration of ammonia is limited solely by the saturation of the solution, for example saturated synthesis solutions under pressure may contain up to about 30% by weight of $NH_3$. It is preferred to use solutions containing up to about 28% by weight of $NH_3$ under normal pressure.

The particular synthesis solution may contain ketones, depending upon the molar ratio in which the reactants were used in the synthesis stage. In most processes, however, only up to about 2 molar excesses of ketone, based on total hydrazine, are present.

The particular synthesis solution may also contain salt-like compounds which are particularly favorable to working up. The salt-like compounds used are those which are used during synthesis in conventional processes or which are formed during the reaction. In general terms, they are salts of inorganic or organic acids or hydroxides of the metals of Main Groups I and II of the Periodic System and of ammonia which may even be alkyl-substituted. The following salts are mentioned by way of example: chlorides, sulfates, phosphates, nitrates, carbonates, carbamates, borates, arsenates, selenates, hydrogen carbonates, chlorates, acetates, propionates, cyanates, cyanides, methanesulfonates, methanephosphonates, phosphonates, oxalates, fumarates, ethylenediaminetetraacetates or mixtures thereof. However, the process according to the invention is by no means dependent for its application upon the presence of certain salts or salt mixtures. There are solubility limits to the salt concentration. Solutions with a salt content of about 5 to 25% by weight are preferred.

The particular synthesis solution may contain alcohols with 1 to about 4 carbon atoms which are added to homogenize the reaction mixture, for example in accordance with German Offenlegungsschrift No. 2,127,229, for example methanol, ethanol, propanol, etc.

The particular synthesis solution may contain the extractants used for extraction, preferably the higher alcohols with from 5 to about 18 carbon atoms, when, for example in continuous working, unreacted reactants such as acetone and $NH_3$ are recycled and the extractants enter the synthesis stage. They may be present in a concentration of up to about 5% by weight.

In addition to the already mentioned components, the particular synthesis solution may also contain organic compounds which were either added in excess or are formed during synthesis, for example nitriles, esters, imides or amides such as those which accumulate in conventional processes using hydrogen peroxide.

In one special embodiment, the synthesis solutions contain hydrazones, ketazines, ketones, for example acetone, dimethyl hydrazone and dimethyl ketazine, ammonia, salt-like compounds and simple organic compounds such as acetamide and methanol, and optionally the extractants as well. Synthesis solutions containing acetone, dimethyl ketazine, dimethyl hydrazone, ammonia and salt-like compounds, for example NaCl or $NH_4Cl$, are particularly suitable.

The process according to the invention for working up the aqueous synthesis solutions consists of several process stages. In the first stage, the organonitrogen compounds of the synthesis solutions are extracted with organic solvents, followed by the removal of ammonia from the aqueous and organic phase. In the second stage, the extractant is separated off from the organonitrogen compound by any one of a number of different possible methods. In the third stage, the organonitrogen compounds are split into the components ketone and hydrazine hydrate or hydrazinium salts.

Various embodiments of the process according to the invention are described hereinbelow with reference to the accompanying drawings, wherein.

Figure 1:
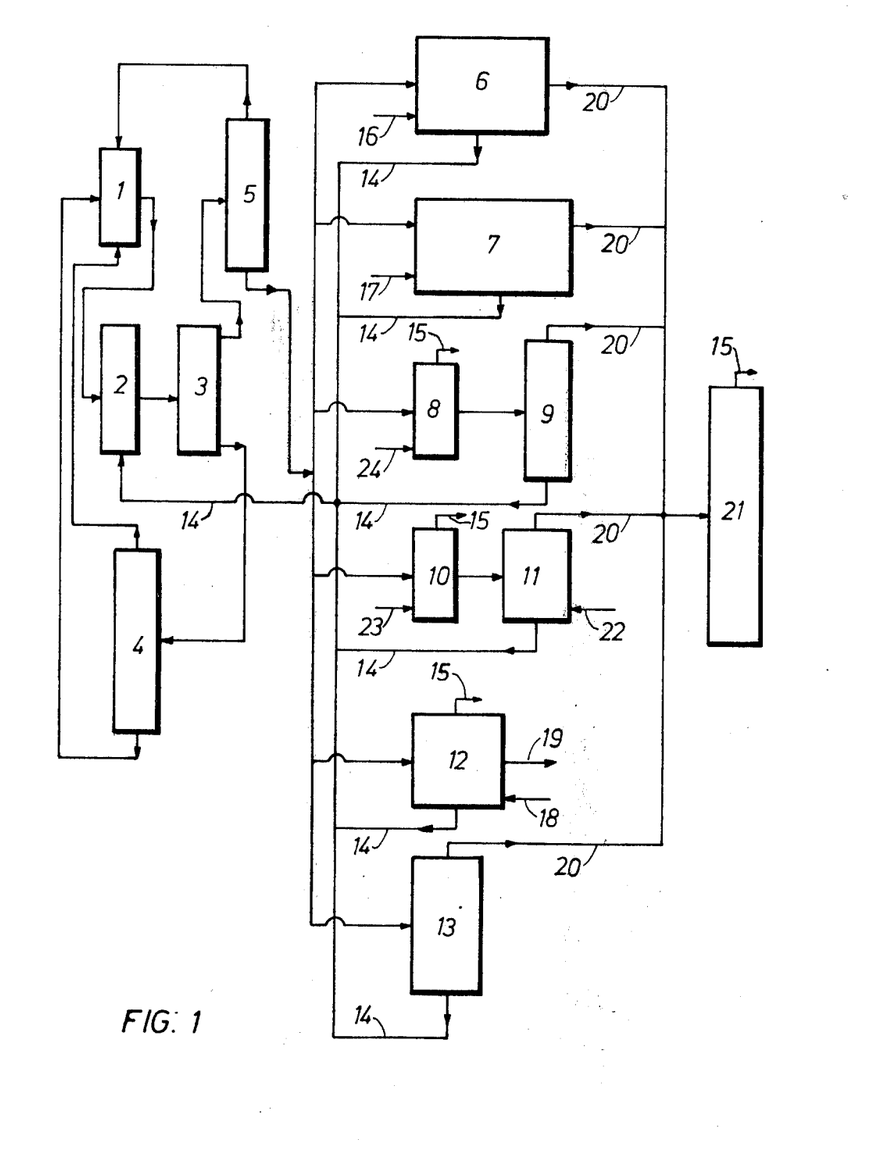
FIG. 1 is a flow sheet of processes for producing, extracting and recovering organonitrogen compounds compounds in accordance with the present invention.

Referring now more particularly to FIG. 1, the reference numerals used have the following meanings: 1 = synthesis reactor, 2 = extractor, 3 = separator, 4, 5, 8, 9, 10, 13 = columns, 6, 7, 11 = extractor + separator, 12 = reactor, 14 = extractant recycling, 15 = ketone, 16 = water input, 17 = hydrazine-containing water, 18 = aqueous acids, 19 = hydrazinium salts, 20 = input of organic hydrazine derivatives into hydrolysis reactor, 21 = hydrolysis reactor, 22, 23, 24 = water inputs.

The synthesis solution to be worked up is transferred from the synthesis reactor 1 to the extractor 2. In the extractor 2, the synthesis solution is mixed with the organic extractant and optionally with ketone. After phase separation in the separator 3, the aqueous phase (raffinate) is introduced into the column 4 for recycling ammonia. $NH_3$ leaves from the head, while an ammonia-free aqueous solution containing salt-like compounds and other non-extracted components leaves the sump of the column. This aqueous solution may be further worked up and optionally delivered to the synthesis reactor.

The extract enters the column 5 in which, in addition to ammonia, other readily volatile components, for example methanol, ethanol, ethyl acetate or acetonitrile, are distilled off overhead and may be recycled. The mixture flowing off from the column 5, containing the extractant, hydrazone, ketazine, optionally ketone and optionally other organic components, may be further treated by various methods, of which 6 variants are described below.

*a*. Re-extracting the mixture with water in the extractor and separator 6, with the proviso that hydrazone and ketazine are primarily re-extracted in the form of ketazine.

b. Re-extracting the mixture with hydrazine-containing water in the extractor and separator 7, with the proviso that hydrazone and ketazine are primarily re-extracted in the form of hydrazone.

c. Partially hydrolyzing the mixture with water in column 8, with the proviso that the ketone formed is continuously removed from the equilibrium mixture until the mixture predominantly contains hydrazone, and subsequently distilling off the hydrazone in column 9.

d. Partially hydrolyzing the mixture with water in column 10 and subsequently re-extracting the hydrazone in the extractor and separator 11.

e. Contacting the mixture with acid HX and water in order to convert hydrazone and ketazine into the salts of hydrazine $(N_2H_5)X$ and $(N_2H_6)X_2$, with liberation of ketone, in the reactor 12, followed by working up of both phases in an extractor and separator (not shown in the drawing) and a column (not shown in the drawing) into hydrazine salts and ketone, and recycling the extractant.

f. Distilling the mixture in column 13, with the proviso that hydrazone and ketazine are primarily distilled off in the form of ketazine together with $H_2O$, and the extractant recycled.

In variants (a), (b), (d) and (e), any aqueous solutions leaving stages 6, 7, 11 and 12 may be subjected to a stripping stage in order to remove dissolved extractant. In all variants, the extractant may be recycled through 14. The preferred embodiments of the process according to the invention consist of a combination of extraction with variants (e) and (f).

After the extractant has been separated off from the organic hydrazine derivatives in accordance with variants (a), (b), (c), (d) and (f), the organic hydrazine derivatives, introduced through 20, may be split up in 21 into the components ketone and hydrazine hydrate or hydrazinium salt by known methods, for example by pressure hydrolysis.

The process according to the invention may be carried out continuously or in batches, although it is preferably carried out continuously.

The extraction stage is based on liquid-liquid extraction. Intimate mixing of the synthesis solution with the extractant in the extractor 2 may be achieved, like phase separation in the separator 3, by shaking, stirring or other suitable measures using machines known per se, for example of the mixer-settler type or of the column extractor type.

Column extractors have proved to be particularly suitable by virtue of their rapid mass transfer and high throughput.

The liquid-liquid extraction is best carried out in several stages. In order to determine the theoretical number of stages, a predetermined volume of the synthesis solution is intensively mixed several successive times with the same volume of extractant, and the hydrazine left in the raffinate is determined, taking into account the changes in volume. Hydrazine means total hydrazine in the form of hydrazone + ketazine. The data in the Examples also relate to hydrazine in the form of hydrazone + ketazine unless otherwise stated. The hydrazine is best determined by iodometric titration in a medium containing sodium hydrogen carbonate after boiling down the extractant and acetone in a strong acid, or by spectroscopic methods, such as proton nuclear resonance or gas chromatography.

The yield of hydrazine per stage, i.e. the hydrazine in the form of hydrazone + ketazine which is extracted per stage, and the total yield over all the stages, can be calculated from the result obtained. Extraction is continued by the method described until the aqueous phase contains less than about 0.005 mole of hydrazine per liter.

The number of stages required for obtaining the maximum total yield is dependent upon a number of factors, of which the most important are salt content, $NH_3$-concentration, concentration of hydrazine, hydrazone, ketazine, molar ratio of total hydrazine to ketone, temperature and pressure.

A high salt content and/or a high concentration of ammonia in the synthesis solution generally provide high yields of hydrazine per stage, in some cases amounting to more than about 90% per stage. Experience has shown that, with ammonia concentrations of more than about 5% by weight, it is best to apply relatively low temperatures of the order of $-10°$ C to $50°$ C where extraction is carried out under normal pressure. Generally extraction may be carried out at temperatures in the range of from $-10°$ C to $100°$ C. Where the synthesis solution contains high concentrations of ammonia, it is important to ensure that the ammonia remains in solution if high yields are to be obtained. This can be done by working under pressure which additionally improves the yields per stage. The pressure under which the process is carried out for keeping ammonia in solution may be in the range of from 1 to 10 atmospheres, although pressures in the range of from 1 to 3 atmospheres are preferred. The concentration of hydrazine, hydrazone and ketazine and mixtures thereof may be between about 0.001 mole/1 and 5 moles/1, based on total hydrazine. Relatively high concentrations are preferred.

The molar ratio of ketone to total hydrazine, which qualitatively reproduces the molar distribution of hydrazine : hydrazone : ketazine, is of particular significance. If the ratio of ketone to total hydrazine is $\leq 1$, both hydrazine and hydrazone are present. Where the ratio is 1, hydrazone only is present and, where the ratio is between 1 and 2, hydrazone and ketazine are present. Where the ratio of ketone to total hydrazine is $\geq 2$, ketazine is present. Since the extraction coefficient increases drastically in the order $N_2H_4$, hydrazone, ketazine (thus where extraction is carried out in a single stage, 99.2% of the hydrazine, 77% of the dimethyl hydrazone and only 27% of the dimethyl ketazine remain in the aqueous phase), it is important to ensure that a molar ratio of at least 1 is guaranteed for extraction. However, better yields are obtained with molar ratios of from 1 – 2 to 2 during extraction. Accordingly, appropriate quantities of ketone, preferably acetone can be added before or during extraction, the particular phase to which the ketone is added being of no fundamental significance, preferred to the organic phase.

A maximum yield should be obtained with a molar ratio of acetone to total hydrazine of 2, i.e. in the presence of pure dimethyl ketazine. However, this is only conditionally the case. It is known that dimethyl ketazine forms the following hydrolysis equilibrium (equation 1):

(1)

in which 5% of the ketazine is present as hydrazone in 1-molar solution at 20° C. The equilibrium is naturally dependent upon the factors referred to above. Accordingly, in a preferred embodiment of the process according to the invention, extraction is carried out in the presence of an excess of ketone, especially acetone, with a molar ratio of ketone to total hydrazine of 2. In this way, the number of stages required to obtain a maximum total yield is reduced by a factor of approximately 2.

Extraction may be carried out with a molar ratio of ketone to total hydrazine of about 1 to 10, preferably about 1.5 to 5 and, with particular preference, about 2 to 2.5. With molar ratios of ≧ 1 in the synthesis solution, it is best to add the ketone during extraction because, in this way, the excess of ketone, i.e. ketone : total hydrazine > 2, is kept low despite an optimum total yield. In cases where extraction is carried out in stages, for example in an apparatus of the mixer-settler type, this is achieved by distributing the quantity of acetone required over the individual stages. With a molar ratio of ketone to total hydrazine of 1.8–2 for example, distribution over the individual stages is obtained by adding only 10% of the total quantity of ketone in the first stage, 20 to 80% in the second stage and the rest in the third stage, so that the extract ultimately has a molar ratio of ketone to total hydrazine of greater than 2. However, in cases where extraction is carried out on the countercurrent principle, for example in a countercurrent extraction column, it is better to add the ketone to the extractant in such a way that the extract running off from the column has a molar ratio greater than 2.

In cases where the synthesis solution has molar ratios of ketone to total hydrazine of from 0 to 1, an addition of ketone is best made to the synthesis solution in order to achieve a molar ratio of approximately 1. More ketone is then added during extraction.

The readjustment of the position of the hydrolysis equilibrium in accordance with equation 1 brought about by the addition of acetone takes less than about 5 minutes. In this process, the separation times are between about 10 seconds and 10 minutes according to temperature and salt content. Emulsions do not occur.

The volume ratio, volume (aqueous phase) : volume (extractant), should be greater than 1 in order to obtain maximum yields and maximum efficiency of the extractant. In the context of the invention, volume is the volume of the particular phase over all the stages. The volume ratio is preferably greater than about 2. It is governed by the concentration of hydrazine in the form of hydrazine + ketazine in the synthesis solution, by the type of extractant used, by the quantitative water uptake of the extractant, by the purpose for which the extract is to be used and by the type of extraction apparatus used. Generally speaking, the ratio is preferred to be higher in relatively dilute hydrazine solutions than in fairly concentrated solutions.

In addition to hydrazone and ketazine, the extracts may also contain acetone, ammonia, water, optionally dissolved salt-like compounds and organic components. Ammonia is co-extracted depending upon its concentration in the aqueous phase, although the extract contains at most only about 5% by weight of ammonia. The salt content of the extract should be between about 1 and 100 ppm although, in the case of sodium chloride, it is between about 10 and 20 ppm. The water content is governed by the type of extractant used, by temperature, by the concentration of ammonia, but above all by the ketazine and hydrazone contents. For example, there is 3.1% by weight of water in 2-ethyl hexanol containing 4.8% by weight of dimethyl ketazine at 20° C, and 6.9% by weight of water in 2-ethyl hexanol containing 37.6% by weight of ketazine at 20° C. The maximum possible water concentration, which depends upon the particular parameters, may readily be determined by subjecting a water-free mixture of substances to turbidity titration with water.

The concentration of ketazine and hydrazone in the extract is governed by their respective concentrations in the synthesis solution, by the volume ratio, by the quantity of ketone and by temperature. It can be between about 0.01 and 5 moles/l. High concentrations are preferred, providing they do not adversely affect yield. Extracts containing from 0.8 to 0.9 mole of ketazine per liter are obtained from an aqueous solution containing 0.5 mole of ketazine per liter where extraction is carried out with a volume ratio of 2. The enrichment factor in the extract is approximately equal to the concentration of total hydrazine per liter in the synthesis solution multiplied by the volume ratio.

The spent raffinate phase may be freed from ammonia and dissolved extractant by conventional methods. The ammonia and extractant may be recycled. The resulting solution, which may contain less than 500 ppm of total hydrazine and dissolved salts or other hydrophilic components, such as acetone, is also worked up for recycling or discarded. For example, the sodium chloride solutions may be worked up by electrolysis into hypochlorite-containing solutions or acetamide by thermal dehydration into acetonitrile according to conventional methods.

Ammonia is quantitatively removed from extracts containing ammonia. If the extracts additionally contain other readily volatile components, of the type which occur for example in conventional processes for the production of hydrazine using $H_2O_2$, for example methanol and acetonitrile, these readily volatile components are either removed with the ammonia or are separately removed after the ammonia by distillation, depending upon their boiling points. It is important to ensure that the extracted organonitrogen compounds largely remain in the extract. The ammonia is best removed by heating the extract in the absence of pressure or under a pressure of about 0.1 to 10 atmospheres, preferably under a pressure of about 0.2 to 5 atmospheres.

The more readily volatile components, whose boiling points should be below those of the ketazine/water azeotropes, are separated off by known methods of distillation with the object of obtaining complete or almost complete separation from the extract.

The ammonia-free extracts may be further worked up by any of the variants (a) to (f) described above which are discussed in more detail hereinbelow with reference to FIG. 1.

Re-extraction with water, introduced through 16, as carried out in the extractor and separator 6, for example in accordance with variant (a), may be carried out in the same way as extraction. In contrast to extraction, ketazine, hydrazone and hydrazine are re-extracted with increasingly better results. Since ketazine can only be re-extracted in several stages, conversion into hydrazone is advisable (variants (b), (c) and (d)), in order to reduce the number of necessary theoretical stages. This is done by methods known per se. Either the ketazine, especially dimethyl ketazine, can be partially hydrolyzed into hydrazone in accordance with equation (2):

(2)

or the following reaction (equation 3) may be used (illustrated with reference by way of example to dimethyl ketazine):

(3)

Partial hydrolysis in accordance with equation (2) is carried out by heating the extract in the presence of water, followed by fractional distillation with removal of acetone. Hydrolysis to form hydrazone in the absence of pressure takes place quickly and completely. The quantity of water required for partial hydrolysis substantially corresponds to the stoichiometric quantity required in accordance with equation (2). However, it is better to use an excess of water. The molar ratio of water to total hydrazine (added during partial hydrolysis) may be between about 1 and 10, preferably between about 1 and 5 and, with particular preference, between about 1 and 3. The water may be added all at once, uniformly distributed over the entire reaction time, or in stages. It is preferred to add the water uniformly and continuously to the extract, accompanied by the continuous removal of ketone. By working continuously, it is possible to avoid the formation of an aqueous phase (a particular characteristic of the process) which would have an adverse effect upon partial hydrolysis both in regard to the hydrolysis velocity and in regard to the composition of the head product.

Partial hydrolysis is preferably carried out at the boiling point of the extract/H₂O mixture, and is accompanied by distillation. It may be carried out at pressures in the range of about 1 to 10 atmospheres and preferably at pressures in the range of about 1 to 5 atmospheres.

In the case of continuous working, the extract is introduced together with water in the lower part of a column 10 or 8 with suitable separation facilities, the ketone is run off at the head 15 while the partially hydrolyzed extract, which may also contain free hydrazine in addition to hydrazone, is continuously run off from the sump. The sump product is subsequently subjected to re-extraction with water in 11, providing ketazine is re-extracted with aqueous hydrazine-containing solution, or the hydrazone is separated off from the extractant by distillation in 9. The extractant is recycled through 14.

Re-extraction of the ketazine with water from the extract in the presence of free hydrazine in accordance with variant (b) in the aqueous phase is exothermic and takes place quickly. The quantity of free hydrazine in water added through 17 to obtain maximum yields should be such that the molar ratio of ketazine (extract) : N₂H₄ (water) is about 0.5 to 4, preferably about 1 to 3. In the case of multiple stage processes, most of the N₂H₄ to be added is preferably distributed over all the stages involved in a quantity corresponding to the molar ratios over all the stages. It can be advantageous to increase the quantity of hydrazine added per stage, for example 10% in the first stage, 15% in the second stage, 20% in the third stage, etc.

In the preferred variant (e), the ammonia-free extract is worked up by contacting the extract with aqueous acids HX, introduced through 18, for example with HCl, H₂SO₄, HBr, acetic acid or oxalic acid. In acid hydrolysis, the salts of hydrazine (N₂H₅)X and (N₂H₆)X₂ are formed in addition to the ketone, depending upon the quantity of acid HX added (19). The hydrazine salts may, for example, be (N₂H₅)Cl, (N₂H₅)Br, (N₂H₅)₂SO₄, (N₂H₆)Cl₂ or (N₂H₆)SO₄. It is also possible, however, to use organic acids or esters with a view to forming organic hydrazides. In cases where maleic acid, for example, is used, it is possible to obtain maleic acid hydrazide by conventional methods.

The quantity of acid used is preferably such that the molar ratio of total hydrazine to HX is about 1 : 1 – 2. Cooling to temperatures of about −20 to +50° C is advisable because otherwise 3,3,5-triorganyl pyrazolines are readily formed. The concentration of the acids is between about 5 and 50% by weight and preferably between about 10 and 35% by weight.

The ketone liberated during acid hydrolysis from ketazine or hydrazone is distributed in both phases, for example acetone in water/2-ethyl hexanol as a distribution factor of approximately 1. The preferred embodiment of acid hydrolysis is the formation of water-soluble hydrazine salts, such as (N₂H₅)₂SO₄, followed by concentration of the aqueous phase by evaporation, for example in a falling-film evaporator, dissolved ketone, extractant and water being distilled off and dry hydrazine salt or concentrated, aqueous solutions being obtained. Ketone is separated off from the organic phase by distillation using known methods and the extractant is recycled through 14.

Another preferred embodiment of the process according to the invention for working up synthesis solutions in the production of hydrazine comprises extraction, followed by fractional distillation, of the ammonia-free water-containing extract in accordance with variant (f). Following removal of the ammonia and readily volatile components, if any, the extract contains the extractant, water, ketazine, hydrazone and, optionally, ketone. The extractants used for this embodiment are preferably the higher alcohols ROH referred to earlier on. It is preferred to subject an extract containing 2-ethyl-hexanol as extractant, also water, dimethyl ketazine, dimethyl hydrazone and acetone, to the fractional distillation stage. The quantitative composition of the extract is governed by the way in which extraction is carried out and by the following removal of ammonia. The object of the fractional distillation stage is to separate off by distillation the ketone, hydrazone, ketazine and water, but in particular the aforementioned organonitrogen compounds of acetone, from the extractant which may again be recycled through 14 for extraction. Distillation is optimal when the head product contains hardly any extractant and when there is a substantially quantitative recovery of water, ketone, hydrazone and ketazine from the distillate.

The column 13 consists of the sump, the separating section, the inlet for the extract, the concentrating section and the head section. Sieve plates or bubble trays or conventional devices for improving the separation factor may be present in order to improve the separation effect. The column is operated in such a way that the organic extract is introduced into the column at the point and at the temperature which corresponds to the composition and temperature of the extract. Distillation is best carried out under a pressure of about 1 to 760 mm Hg preferably under a pressure of about 10 to 200 mm Hg and, with particular preference, under a pressure of about 50 to 150 mm Hg.

The particularly desirable extractant-free head product is only obtained under special conditions which restrict the choice of the extractant in variant (f) and which only allow particular concentrations of ketazine. In the present context, the term ketazine is used for extracts and distillates which have a molar ratio of total ketazine to ketone of about 1 : 1.8 to 1 : 3. It is preferred to use acetone and its compounds with hydrazine. The extractants used are extractants whose boiling point or that of its azeotrope with water is higher than that of the ketazine or its azeotrope with water. Accordingly, the higher alcohols, and especially the preferred alcohols, are used in cases where extraction is followed by working up by distillation. An extractant-free head product is obtained when the total quantity of water in the extract is smaller than the quantity of water which may be associated with the water content of the azeotrope of the ketazine present in the extract. In the case of dimethyl ketazine, the molar ratio of $H_2O$ : ketazine of the azeotrope $H_2O$/ketazine is about 5 : 1, so that, in order to obtain an extractant-free head product, fractional distillation may be carried out up to a molar ratio of $H_2O$ : dimethyl ketazine   5 : 1 in the extract. If this limit is exceeded, the distillate contains increasing quantities of extractant. For this reason, it is best only to use extractants of the kind which, like the preferred alcohols referred to above, are only able to dissolve a little water. In the pressure range of about 1 to 760 mm Hg, this limit is substantially unaffected by pressure. The composition of the head product corresponds to the composition arising out of the quantity of ketazine and $H_2O$ in the extract. In simple terms, the fractional distillation stage is a separation of the two azeotropes extractant/$H_2O$ and ketazine/$H_2O$. In some cases, the higher ketones and their organonitrogen compounds with more than 3 carbon atoms can further complicate distillation. Accordingly, acetone is preferably used as the ketone in this case. In cases where 2-ethyl-hexanol, for example, is used as the extractant, the boiling point of its azeotrope with water is 99° C, while the boiling point of the dimethyl ketazine/$H_2O$ azeotrope is about 95° C. Accordingly, it is best to apply the criteria discussed above in selecting the extractant for its distillation properties as well. 2-Ethyl-hexanol is particularly suitable.

Extracts containing water and ketazine in a molar ratio whose water component is greater than the composition of the azeotrope have to be concentrated with ketazine by suitable measures. This can be done, for example, by increasing the volume ratio during extraction or by returning some of the head product to the extraction stage.

Distillation is best carried out continuously, together with extraction and the removal of ammonia.

Figure 2:
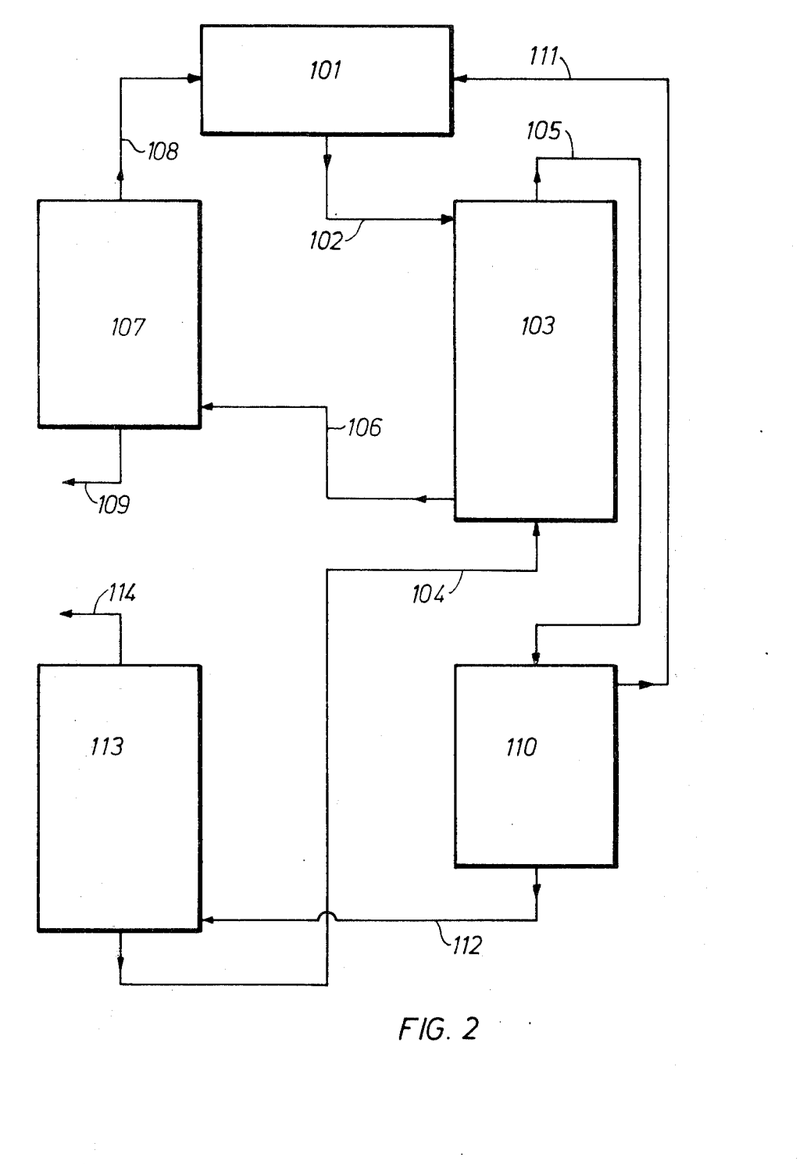
FIG. 2 is a flow sheet of a preferred continuous process in accordance with one of the alternatives shown in FIG. 1.

One continuous embodiment of this preferred process with its extraction section and working up by distillation in accordance with variant (f) into a ketazine/water mixture is shown in FIG. 2, which relates by way of example to a synthesis solution obtained by the Acetone Raschig process with 2-ethyl-hexanol as the extractant.

From the synthesis reactor 101, the synthesis solution containing dimethyl ketazine is introduced through the pipe 102 to the head of a pulsating packed column 103, while at the same time 2-ethyl-hexanol (2-EH) and, optionally, acetone are introduced into the lower part of the packed column 103 through the pipe 104. The extract leaves the extraction apparatus from the head through 105, the raffinate leaving through 106. In the ammonia separation column 107, the raffinate is separated into ammonia, which returns to the reactor 101 through 108, and into the sodium chloride solution which flows off through 109. In the ammonia separation column 110, the extract is freed from ammonia, which re-enters the reactor 101 through 111, and is then pumped through 112 into the distillation column 113. 2-Ethyl-hexanol substantially free from dimethyl ketazine leaves the sump of the column 113, and is fed back into the extraction apparatus through pipe 104. A ketazine-water mixture distills off overhead at 114 and may be subjected to separation by pressure hydrolysis into hydrazine and acetone (not shown) by known methods.

It is also possible to remove the water present in the ketazine/water mixture with suitable entraining agents, whose azeotropes boil below the ketazine and water azeotrope, for example with benzene or chlorinated hydrocarbons, so that water-free organic ketazine solutions are formed and may be used as valuable intermediate products for synthesis.

The working up process according to the invention may be applied to any known "hydrazine synthesis solutions" and gives highly concentrated ketazine solutions. Working up is sparing in its effect and leads to lower losses of acetone and hydrazine coupled with high yields. In addition, the step of separating $NH_3$ from the water phase carried out at the beginning of conventional processes may now be carried out after extraction, thereby eliminating the need to hydrolyze the ketazine into hydrazone during separation of the $NH_3$ and subsequently to convert the hydrazone into ketazine for distillation by known methods.

Another advantage of the process according to the invention is that it is largely unaffected by the concentrations of the hydrazine, hydrazone and ketazine and can still be carried out with very low concentrations of the hydrazine or hydrazone or ketazine.

The process according to the invention is illustrated in the following Examples. The yields are expressed predominantly in mole percent of the quantity used. The compositions of the solutions are predominantly expressed in percent by weight.

EXAMPLE 1(a)

100 ml of an aqueous solution containing sodium chloride with or without ammonia, with dimethyl ketazine or dimethyl hydrazone, was extracted with an alcohol ROH for 30 minutes at 24° C with intensive stirring (magnetic stirrer). The ketazine or hydrazone left in the raffinate (aqueous phase) was iodometrically determined as hydrazine and expressed in mole percent of the quantity used. Table 1 shows dimethyl ketazine and Table 2 shows dimethyl hydrazone.

Table 1

| ROH | % by weight of ketazine | % by weight of NaCl | % by weight of $NH_3$ | mole % of the quantity used in the raffinate |
|---|---|---|---|---|
| n-pentanol | 8.36 | 5 | — | 17.9 |
|  | 8.36 | 5 | 25 | 12.6 |
| cyclohexanol | 8.36 | 5 | — | 17.5 |
|  | 8.36 | 5 | 25 | 12.9 |
| 2-methyl-cyclohexanol | 8.36 | 5 | — | 20.1 |
|  | 8.36 | 5 | 25 | 10.8 |
| 2-ethyl-butanol | 6.0 | 7 | 15 | 10.5 |
| n-octanol | 6.0 | 7 | 15 | 16.3 |
| 2-ethyl-hexanol | 8.36 | 5 | — | 27.0 |
|  | 8.36 | 5 | 25 | 13.6 |
|  | 8.36 | 10 | 22 | 12.7 |
|  | 6.0 | 7 | 15 | 14.5 |
|  | 1.22 | 22.5 | 2.4 | 19.0 |
| 3,3,5-trimethyl-hexanol | 8.36 | 5 | — | 27.5 |
|  | 8.36 | 5 | 25 | 17.2 |
| 3,5,5-trimethyl-hexanol | 6.0 | 7 | 15 | 16.4 |
| n-decanol | 6.0 | 7 | 15 | 19.1 |
| n-dodecanol | 6.0 | 7 | 15 | 20.9 |
| mixture: 27% n-hexanol, 40% n-octanol, 33% n-decanol | 8.36 | 5 | — | 27.1 |
|  | 8.36 | 5 | 25 | 16.1 |

Table 2

| ROH | % by weight of dimethyl hydrazone | % by weight of NaCl | % by weight of $NH_3$ | mole % of the quantity used in the raffinate |
|---|---|---|---|---|
| n-pentanol | 9.0 | 5 | — | 66.0 |
|  | 9.0 | 5 | 25 | 49.1 |
| cyclohexanol | 9.0 | 5 | — | 61.5 |
|  | 9.0 | 5 | 25 | 45.8 |
| 2-methyl-cyclohexanol | 9.0 | 5 | — | 65.4 |
|  | 9.0 | 5 | 25 | 55.6 |
| 2-ethyl hexanol | 9.0 | 5 | — | 77.4 |
|  | 9.0 | 5 | 25 | 64.4 |
| 3,3,5-trimethyl-hexanol | 9.0 | 5 | — | 79.3 |
|  | 9.0 | 5 | 25 | 68.6 |
| mixture | 9.0 | 5 | — | 74.0 |
|  | 9.0 | 5 | 25 | 64.0 |

EXAMPLE 1(b)

100 ml of an aqueous solution containing sodium chloride, with or without ammonia, with dimethyl ketazine or dimethyl hydrazone, was extracted with a lower chlorinated hydrocarbon for 30 minutes at 24° C with intensive stirring. The dimethyl ketazine or hydrazone left in the raffinate was iodometrically determined as hydrazine and expressed as a percentage of the quantity used. Table 3 shows dimethyl ketazine and Table 4 shows dimethyl hydrazone.

Table 3

| Chlorinated hydrocarbon | % by weight of dimethyl ketazine | % by weight of NaCl | % by weight of $NH_3$ | mole % of the quantity used in the raffinate |
|---|---|---|---|---|
| $CH_2Cl_2$ | 8.36 | 5 | — | 12.2 |
| $CHCl_3$ | 8.36 | 5 | — | 7.3 |
| $CCl_4$ | 8.36 | 5 | — | 28.8 |
| $C_2H_4Cl_2$ | 8.36 | 5 | — | 20.5 |
| $C_2HCl_3$ | 8.36 | 5 | — | 20.3 |
| $C_3H_3Cl_5$ | 8.36 | 5 | — | 19.7 |
| $CH_2Cl_2$ | 8.36 | 5 | 25 | 9.8 |
| $CHCl_3$ | 8.36 | 5 | 25 | 5.5 |
| $C_2H_4Cl_2$ | 8.36 | 5 | 25 | 11.3 |
| $C_2HCl_3$ | 8.36 | 5 | 25 | 10.6 |
| $C_3H_3Cl_5$ | 8.36 | 5 | 25 | 12.6 |

Table 4

| Chlorinated hydrocarbon | % by weight of dimethyl hydrazone | % by weight of NaCl | % by weight of $NH_3$ | mole % of the quantity used in the raffinate |
|---|---|---|---|---|
| $CH_2Cl_2$ | 9.0 | 5 | — | 91.2 |
| $CHCl_3$ | 9.0 | 5 | — | 77.5 |
| $CCl_4$ | 9.0 | 5 | — | 91.3 |
| $C_2H_4Cl_2$ | 9.0 | 5 | — | 81.0 |
| $C_2HCl_3$ | 9.0 | 5 | — | 87.0 |
| $C_3H_3Cl_5$ | 9.0 | 5 | — | 70.0 |
| $CH_2Cl_2$ | 9.0 | 5 | 25 | 64.4 |
| $CHCl_3$ | 9.0 | 5 | 25 | 46.7 |
| $C_2H_4Cl_2$ | 9.0 | 5 | 25 | 70.8 |
| $C_2HCl_3$ | 9.0 | 5 | 25 | 79.0 |
| $C_3H_3Cl_5$ | 9.0 | 5 | 25 | 63.8 |

EXAMPLE 1(c)

The procedure was as in Example 1(b), except that benzene derivatives were used as extractants instead of the chlorinated hydrocarbons (5% by weight of NaCl). The results are shown on Table 5.

Table 5

| $R_1$ | $R_2$ | $R_3$ | % by weight of $NH_3$ | % by weight of dimethyl ketazine | mole % in the raffinate | % by weight of dimethyl hydrazone | mole % in the raffinate |
|---|---|---|---|---|---|---|---|
| H | H | $NH_2$ | — | 8.36 | 16.0 | 9.0 | 58.1 |
| H | H | H | — | 8.36 | 27.9 | 9.0 | 90.1 |
| H | H | Cl | — | 8.36 | 28.4 | 9.0 | 89.4 |
| H | H | CN | — | 8.36 | 30.2 | 9.0 | 89.3 |

Table 5-continued

| $R_1$ | $R_2$ | $R_3$ | % by weight of $NH_3$ | % by weight of dimethyl ketazine | mole % in the raffinate | % by weight of dimethyl hydrazone | mole % in the raffinate |
|---|---|---|---|---|---|---|---|
| H | H | $CH_3$ | — | 8.36 | 33.9 | 9.0 | 90.3 |
| H | H | $OCH_3$ | — | 8.36 | 34.4 | 9.0 | 87.6 |
| H | H | Br | — | 8.36 | 35.2 | 9.0 | 90.6 |
| H | H | $NO_2$ | — | 8.36 | 36.4 | 9.0 | 87.0 |
| H | 1-$NH_2$ | 3-Cl | — | 8.36 | 10.4 | 9.0 | 58.4 |
| H | 1-$NH_2$ | 2-Cl | — | 8.36 | 13.8 | 9.0 | 65.3 |
| 1-Cl | 2-$CH_3$ | 3-$NH_2$ | — | 8.36 | 14.6 | 9.0 | 64.0 |
| H | 1-$NH_2$ | 2-$CO_2CH_3$ | — | 8.36 | 27.4 | 9.0 | 74.1 |
| H | 1-$NH_2$ | 2-$OCH_3$ | — | 8.36 | 29.8 | 9.0 | 77.9 |
| H | 1-Cl | 2-Cl | — | 8.36 | 32.5 | 9.0 | 89.6 |
| H | 1-$CH_3$ | 2-$NO_2$ | — | 8.36 | 40.7 | 9.0 | 97.6 |
| H | H | $NH_2$ | 25 | 8.36 | 12.1 | 9.0 | 92.1 |
| H | H | H | 25 | 8.36 | 14.1 | 9.0 | 84.6 |
| H | H | Cl | 25 | 8.36 | 14.6 | 9.0 | — |
| H | H | CN | 25 | 8.36 | 16.5 | 9.0 | 70.2 |
| H | H | $CH_3$ | 25 | 8.36 | 16.7 | 9.0 | 87.8 |
| H | H | $OCH_3$ | 25 | 8.36 | 15.7 | 9.0 | 81.4 |
| H | H | Br | 25 | 8.36 | 14.9 | 9.0 | 83.6 |
| H | H | $NO_2$ | 25 | 8.36 | 19.7 | 9.0 | 79.8 |
| H | 1-$NH_2$ | 3-Cl | 25 | 8.36 | 5.6 | 9.0 | 30.8 |
| H | 1-$NH_2$ | 2-Cl | 25 | 8.36 | 8.7 | 9.0 | 47.2 |
| 1-Cl | 2-$CH_3$ | 3-$NH_2$ | 25 | 8.36 | 7.7 | 9.0 | 44.5 |
| H | 1-$NH_2$ | 2-$CO_2CH_3$ | 25 | 8.36 | 12.2 | 9.0 | 56.8 |
| H | 1-$NH_2$ | 2-$OCH_3$ | 25 | 8.36 | 18.7 | 9.0 | 55.9 |
| H | 1-Cl | 2-Cl | 25 | 8.36 | 18.3 | 9.0 | 88.6 |
| H | 1-$CH_3$ | 2-$NO_2$ | 25 | 8.36 | 19.5 | 9.0 | 80.7 |

EXAMPLE 1(d)

A mixture of 40 g of acetamide, 40 g of dimethyl ketazine and 120 g of water was extracted with 205 ml of 2-ethyl-hexanol for 30 minutes at a temperature of 24° C. The raffinate still contained 37.2% of the dimethylketazine used, while the extract contained 1.17% by weight of acetamide, 5.85% of the acetamide used.

EXAMPLE 1(e)

A mixture of 35 g of ammonium carbonate, 40 g of dimethyl ketazine and 200 g of water was extracted with 265 ml of 2-ethyl-hexanol. 18.5% of the ketazine used remained in the raffinate. By contrast, the extract contained only 0.45% of the carbonate used.

EXAMPLE 1(f)

An aqueous solution containing a salt and dimethyl ketazine was extracted once at 23° C with an equal volume of 2-ethyl-hexanol (Table 6).

Table 6

| Salt | Composition of the solution % by weight | | | | Dimethyl ketazine in mole % in the raffinate |
|---|---|---|---|---|---|
| | $H_2O$ | salt | ketazine | $NH_3$ | |
| $NH_4Cl$ | 86.5 | 8.65 | 4.85 | — | 25.9 |
| $Na_2SO_4$ | 86.5 | 8.65 | 4.85 | — | 14.3 |
| $NH_4$-acetate | 86.0 | 8.6 | 4.8 | 0.6 | 24.8 |

EXAMPLE 2

100 ml of an aqueous solution containing 6.0% by weight of dimethyl ketazine, 7% by weight of NaCl and 15% by weight of ammonia were extracted for 30 minutes at various temperatures (T° C) with 100 ml of 2-ethyl-hexanol (Table 7).

Table 7

| T° C | 0 | 20 | 45 | 60 | 75 |
|---|---|---|---|---|---|
| mole % of the quantity used in the raffinate | 19.3 | 15.3 | 10.8 | 10.3 | 10.7 |

EXAMPLE 3

500 ml of a 0.54 molar dimethyl ketazine solution containing 7% by weight of NaCl and 15% by weight of $NH_3$, were thoroughly extracted several times at 20° C with 2-ethyl-hexanol (volume ratio of the phases 1 : 1; extraction time 30 minutes; separation time ~2 minutes [Table 8]).

Table 8

| Stage | Extract yield % ketazine/ stage | yield % of the quantity used | raffinate hydrazine concentration mole/l | Extract % $NH_3$ | ppm NaCl |
|---|---|---|---|---|---|
| 1 | 85.5 | 85.5 | 0.091 | 8.5 | 15 |
| 2 | 65.0 | 95.0 | 0.0346 | | 18 |
| 3 | 55.4 | 97.8 | 0.0162 | | 10 |
| 4 | 34.8 | 98.5 | 0.0091 | | |
| 5 | 34.5 | 99.0 | 0.0075 | | |
| 6 | 35.8 | 99.4 | 0.0051 | | |
| 7 | 15.0 | 99.6 | 0.0045 | | |

EXAMPLE 4

500 ml of a 0.11 molar dimethyl ketazine solution, containing 22.5% of NaCl and 2.4% of $NH_3$, were thoroughly extracted at a temperature of 20° C with 2-ethyl-hexanol under the same conditions as in Example 3 (Table 9).

Table 9

| Stage | Extract yield % ketazine/ stage | Extract yield % of the quantity used | raffinate hydrazine concentration mole/l |
|---|---|---|---|
| 1 | 81 | 81 | 0.0215 |
| 2 | 50.5 | 90.5 | 0.0108 |
| 3 | 41.1 | 94.2 | 0.0065 |
| 4 | 35.7 | 96.0 | 0.0042 |

EXAMPLE 5

500 ml of a 0.5 molar dimethyl ketazine solution containing 7% by weight of NaCl and 15% by weight of $NH_3$ were thoroughly extracted with 2-ethyl-hexanol in the presence of acetone at a temperature of 20° C. Acetone was added to both phases before extraction of the suspension (Table 10).

Table 10

| K | K'[1] | stage | % of total quantity of acetone added | % ketazine stage in extract[2],[3] | yield % ketazine |
|---|---|---|---|---|---|
| 4.5 | 2.222 | 1 | — | 87.2 | 87.2 |
| | | 2 | 78 | 82.05 | 97.75 |
| | | 3 | 22 | 87.6 | 99.62 |
| 3.38 | 2.298 | 1 | 50 | 86.95 | 96.95 |
| | | 2 | 33 | 82.9 | 98.0 |
| | | 3 | 17 | 75.2 | 99.5 |
| 2.76 | 2.363 | 1 | — | 86.1 | 86.1 |
| | | 2 | 63 | 81.5 | 97.5 |
| | | 3 | 37 | 85.8 | 99.65 |

(Extraction time 0.5 h; T=20° C; K=molar ratio $\frac{\text{ketazine}}{\text{acetone added}}$)

[1] K' = molar ratio $\frac{\text{total acetone}}{\text{hydrazine}}$

[2] ~13 ppm NaCl in extract
[3] separation time 1,5 – 3,15 minutes

EXAMPLE 6

500 ml of the ketazine solution described in Example 5 were extracted once (stage 1) with 500 ml of 2-ethyl-hexanol in the absence of acetone over various periods (Table 11).

Table 11

| Extraction time (minutes) | Yield: % ketazine in extract | separation time (minutes) |
|---|---|---|
| 5 | 85.05 | 1.25 |
| 10 | 84.4 | 1.5 |
| 15 | 85.1 | 1.75 |
| 20 | 85.1 | 1.75 |

EXAMPLE 7

500 ml of an aqueous solution obtained after 5 minutes in accordance with Example 6 (raffinate stage 1) were extracted with 500 ml of 2-ethyl-hexanol containing acetone in dependence upon the extraction time of the second stage (Table 12).

Table 12

| Extraction time (minutes) | Yield: % ketazine in extract | separation time (minutes) |
|---|---|---|
| 5 | 75.2 | 0.75 |
| 10 | 74.9 | 0.75 |
| 15 | 74.7 | 1.0 |
| 20 | 77.5 | 1.25 |

(K = 0.68; K' = 3.47)

EXAMPLE 8

Acetone was added to 500 ml of a raffinate obtained after 5 minutes in accordance with Example 6 (stage 1); K = 0.68, K' = 3.47, followed after various residence times by extraction with 500 ml of 2-ethyl-hexanol (stage 2) [Table 13]).

Table 13

| Residence time of aqueous phase with acetone (minutes) | Yield % ketazine in extract | Separation time (minutes) |
|---|---|---|
| 5 | 78.4 | 0.25 |
| 10 | 79.5 | 0.75 |
| 15 | 81.3 | 0.75 |
| 20 | 81.3 | 0.75 |

EXAMPLE 9

500 ml of the ketazine solution described in Example 4 were thoroughly extracted with 2-ethyl-hexanol in the presence of acetone (K = 0.91; K' = 3.11). Separation time = 1 minute; acetone was added to the aqueous phase. (Table 14).

Table 14

| Stage | % of total quantity of acetone added | % ketazine/ stage in extract | yield % ketazine in extract |
|---|---|---|---|
| 1 | 0 | 8.51 | 85.1 |
| 2 | 40 | 64.6 | 95.8 |
| 3 | 40 | 60.3 | 97.8 |
| 4 | 20 | 78.5 | 99.5 |

EXAMPLE 10

A solution containing 0.538 – 0.556 mole/l of total hydrazine, 7% by weight of NaCl and 15% by weight of $NH_3$, which had been prepared by the Acetone-Raschig process, was continuously extracted with 2-ethyl-hexanol according to the countercurrent principle in a pulsating packed column. (Test-period 3 – 6h). The total volume ratio of ketazine solution to 2-ethyl-hexanol was 2 : 1 (Table 15). Volume of column when empty: 3.6 liters; volume of column when filled with 6 mm diameter Raschig rings: 2.27 liters; diameter of column: 50 mm; height of packing: 120 cm; stroke frequency: 129 strokes/minute; temperature: 20° C; $d_{org}^{20}$= 0.826 – 0.83 $d_{inorg}^{20}$= 0.985; (delivery by twin pump).

Table 15

| Synthesis solution (mole/l) total hydrazine | input (l/h) synthesis solution | 2-EH | Stroke volume (ml/sec) | total hydrazine conc. mole/l in extract | % by weight of dimethyl ketazine in extract[2] | Yield % of total hydrazine |
|---|---|---|---|---|---|---|
| 0.538 | 1.55 | 0.774 | 24.6 | 0.763 | 10.3 | 97.8 |
| 0.56 | 4.0 | 2.0 | 42 | 0.885 | 11.9 | 96.6 |
| 0.556 | 8.0 | 4.0 | 42 | 0.819 | 11.0 | 95.2 |
| 0.552 | 4.0 | 2.0[1] | 28.3 | 0.855 | 11.5 | 98.4 |

[1] 20 ml of acetone/l 2-EH were introduced (K' = 2.35)
[2] organic phase contains 1.25 ± 0.5 % by weight of $NH_3$ Samples of both phases were taken at 30 minute intervals and the ketazine content was determined.

EXAMPLE 11 (Re-extraction)

500 ml of a solution of dimethyl ketazine or hydrazone in 2-ethyl-hexanol in various concentrations were repeatedly re-extracted with distilled water at different temperatures. The volume ratio inorg/org. phase was 1 : 1 in each case (Table 16).

Table 16

| mole of dimethyl ketazine/l | T° C | stage | separation time in minutes | % of total quantity hydrazine* in $H_2O$ extract |
|---|---|---|---|---|
| 0.587 | 20 | 1 | 3 | 38 |
| | | 2 | 3 | 60.9 |
| | | 3 | 60 | 74 |
| | | 4 | 180 | 82.5 |
| | | 5 | 120 | 87.7 |
| | | 6 | 120 | 91.9 |
| 0.605 | 0 | 1 | | 59.2 |
| | | 2 | | 80.3 |
| | | 3 | | 93.9 |
| 0.535 | 40 | 1 | | 29.5 |
| | | 2 | | 52.9 |
| | | 3 | | 63.2 |
| | | 4 | | 71.2 |
| 0.578 | 80 | 1 | | 25.3 |
| | | 2 | | 42.7 |
| | | 3 | | 55.9 |

*hydrazine = dimethyl ketazine:dimethyl hydrazone

| mol of dimethyl hydrazone/l | T° C | stage | % of dimethyl hydrazone in $H_2O$-extract |
|---|---|---|---|
| 1.0 | 20 | 1 | 82.4 |
| | | 2 | 94.5 |

EXAMPLE 12

A mixture of 50 g of dimethyl ketazine 34.8 g of water and 500 g of 2-ethyl-hexanol was boiled for several hours at 110° C, and the acetone formed by hydrolysis was removed at intervals through a 50 cm Spiegel column filled with 6 mm diameter Raschig rings, in conjunction with a fraction divider, until a constant head temperature of an average 58° – 59° C was obtained. The head product had the following average composition: 96.5% of acetone; 1.9% by weight of dimethyl ketazine; 0.8% by weight of 2-ethyl-hexanol; and 0.8% by weight of water. Following the removal of 24.9 g of distillate, which contained 23.23 g of acetone, the degree of hydrolysis for the hydrolysis of dimethyl ketazine into dimethyl hydrazone amounted to 91.2%.

Following the addition of another 5 g of $H_2O$, another 8.4 g of distillate were removed containing 7.38 g of acetone, corresponding to a degree of hydrolysis of 121%, in other words hydrazone was further hydrolyzed to form free hydrazine.

EXAMPLE 13

The solution containing 0.437 mole of total hydrazine obtained in accordance with Example 12 was re-extracted with 100 ml of water. The organic 2-ethyl hexanol phase contained 0.237 mole of hydrazine in the form of dimethyl hydrazone, while the $H_2O$ phase contained 0.2 mole of hydrazine in the form of 0.0964 mole of free hydrazine and 0.1036 mole of dimethyl hydrazone (determined by $^1H$-NMR spectroscopy). This corresponds to a degree of hydrolysis of 122.1%.

EXAMPLE 14

500 ml of a solution of dimethyl ketazine in 2-ethyl hexanol were repeatedly re-extracted with distilled water at 25° C in the presence of hydrazine (the volume ratio between both phases at the beginning of each re-extraction step was 1 : 1). (Table 17).

Table 17

| c | y | stage | % of x | separation time (h) | % $N_2H_4$ */ stage in $H_2O$ extract | % of total quantity of $N_2H_4$ * in $H_2O$ extract |
|---|---|---|---|---|---|---|
| 1.855 | 1.05 | 1 | 100 | — | — | 84.2 |
| 1.965 | 1.25 | 1 | 100 | — | — | 86.5 |
| | | 2 | — | — | — | 97.3 |
| 0.593 | 0.995 | 1 | 100 | 0.1 | 78.0 | 78.0 |
| | | 2 | — | 3 | 53.7 | 90.0 |
| | | 3 | — | 3 | 24.2 | 92.5 |
| | | 4 | — | 1 | 16.9 | 93.8 |
| | | 5 | — | 1 | 15.3 | 94.8 |
| | | 6 | — | 1 | 11.8 | 95.3 |
| 0.588 | 0.995 | 1 | 50 | — | 66.3 | 66.3 |
| | | 2 | 25 | — | 67.3 | 86.0 |
| | | 3 | 13 | — | 67.5 | 93.5 |
| | | 4 | 7 | — | 63.7 | 96.5 |
| | | 5 | 5 | — | 61.0 | 97.9 |
| 0.58 | 1.74 | 1 | 10 | 0.1 | 39.7 | 39.7 |
| | | 2 | 15 | 1 | 46.0 | 65.8 |
| | | 3 | 20 | 1.5 | 55.3 | 82.2 |
| | | 4 | 25 | 2.5 | 67.6 | 91.5 |
| | | 5 | 30 | 3 | 78.7 | 96.8 | c = mole of dimethyl ketazine/l
x = total moles of hydrazine added
$y = \frac{c}{x}$
% of x = proportion of total quantity of hydrazine added to the particular stage
* $N_2H_4$ = dimethyl ketazine + dimethyl hydrazone + hydrazine, but mainly hydrazone

EXAMPLE 14(a)

0.5 mol of 98% sulfuric acid dissolved in 100 ml of water were added dropwise over a period of 15 minutes at 20° C to a mixture of 500 ml of 2-ethyl-hexanol, 56 g (0.5 mole) of dimethyl ketazine, 5.8 g (0.1 mole) of acetone and 200 ml of water. After the acid had been added, the organic phase was separated off. It contained 1% of the hydrazine used. The aqueous phase, which contained a solid phase of hydrazine sulfate, was concentrated to 100 ml by distilling off acetone and 2-ethyl-hexanol. The hydrazine sulfate precipitated was filtered off, washed with a little methanol and dried. A yield of 63 g of $(N_2H_6)SO_4$ was obtained, corresponding to approximately 97%.

EXAMPLE 15

A synthetic 2-ethyl-hexanol extract containing 85.7% by weight of 2-ethyl-hexanol, 10.23% by weight of dimethyl ketazine, 1.04% by weight of $NH_3$ and 3.28% by weight of water was slowly heated over a period of 2.25 hours to a temperature of 111° C. The evolution of ammonia began at around 74° C. The ammonia given off was adsorbed in three flasks filled with 1N hydrochloric acid, and was quantitatively determined by titration with 2N sodium hydroxide.

Following separation of the ammonia, 98% of the total ammonia, 0.04% of the ketazine and 25 mg of 2-ethyl-hexanol were found in the receiver.

EXAMPLE 16

488 ml of a mixture containing 6% dimethyl ketazine, 2.12% water and 91.88% 2-ethyl-hexanol (molar ratio $H_2O$ : dimethylketazine = 2.22) was continuously rectified per hour at 50 mm Hg. The rectification column consisted of an electrically heated evaporator with a capacity of approximately 2 liters, 5 metal-coated columns with a vacuum jacket (30 cm long, 0.5 cm in diameter, packing: 6 mm diameter Raschig rings) with intermediate junctions which additionally serve as tapping points and temperature-measuring zones, and of a water-cooled head. The temperature in the column was measured automatically. $T_1$ = head measuring zone distillate $T_2$, $T_3$, $T_5$ = measuring zones between the columns $T_4$ = input-measuring zone and $T_6$ = sump output. The mixture to be rectified was continuously pumped in at $T_4$ with a temperature of 80° – 95° C and the head product and the water-free and ketazine-free sump were continuously removed. The yield of dimethylketazine was 98% and 94% of water. The column was operated principally on the basis of the temperature readings from the measuring zones $T_1$ – $T_6$, the resulting 2-ethyl-hexanol content of the head product and the total yield (Table 18).

hydrazine and ketone, the improvement which comprises effecting the concentration of the hydrazone and ketazine by extracting the aqueous solution with a substantially water-immiscible higher alcohol with 5 to about 18 carbon atoms whereby the hydrazone and ketazine preferentially enter the water-immiscible higher alcohol, and separating the water-immiscible higher alcohol extract from the aqueous solution.

2. A process as claimed in claim 1, wherein the initial aqueous solution contains hydrazine plus hydrazone plus ketazine in a concentration of about 0.01 to 5 moles/l.

3. A process as claimed in claim 1, wherein the initial aqueous solution contains up to about 28% by weight of ammonia and up to 25% by weight of salts.

4. A process as claimed in claim 1, wherein the initial aqueous solution contains at least one salt selected from the group consisting of sodium chloride, sodium sulfate, ammonium chloride, ammonium sulfate, ammonium carbonate and ammonium carbamate.

5. A process as claimed in claim 1, wherein the initial aqueous solution further contains at least one member selected from the group consisting of an alcohol with from 1 to 4 carbon atoms, an organic nitrile, an ester, an imide and an amide.

6. A process as claimed in claim 1, wherein the initial aqueous solution further contains at least one member selected from the group consisting of methanol, acetonitrile and acetamide.

7. A process as claimed in claim 1, wherein the initial aqueous solution contains up to about 5% by weight of the water-immiscible higher alcohol.

8. A process as claimed in claim 1, wherein the initial aqueous solution also contains hydrazine, and ketone is added thereto to convert the hydrazine to hydrazone or ketazine.

9. A process as claimed in claim 1, wherein the ketone is acetone, wherein the ketazine is dimethylketazine and wherein the hydrazone is dimethylhydrazone.

10. A process as claimed in claim 1, wherein the higher alcohol boils at a temperature above about 150° C under normal pressure, has a solubility in water of less than about 0.1% by weight, dissolves less than about 4% by weight of water and forms an azeotrope with water boiling at a temperature above 99° C, the azeotrope containing less than about 25% by weight of alcohol.

11. A process as claimed in claim 10, wherein the higher alcohol is at least one member selected from the group consisting of 3-methyl-hexanol, 5-methyl-hexanol, 2-ethyl-hexanol, n-octanol, 3,5,5-trimethyl-hexanol, dimethyl-hexanol, 4-ethyl-octanol, tridecanol, i-tridecanol, i-octadecanol, n-nonanol, n-decanol and n-dodecanol.

Table 18

| Throughput 2-EH | Throughput $H_2O$ | (total) dimethyl ketazine | (g) Test period (h) | Temperature measuring zone T | Temperature measuring zone T° C | Column composition % in measuring zone T ketazine | Column composition % in measuring zone T 2-EH | Column composition % in measuring zone T $H_2O$ | acetone |
|---|---|---|---|---|---|---|---|---|---|
| 2049 | 47.3 | 134 | 5.5 | 1 | 36 | 77 | — | 23 | — |
|  |  |  |  | 2 | 49 | 97.3 | — | 2.0 | 0.4 |
|  |  |  |  | 3 | 54 | 92.4 | 4.5 | 2.5 | 0.6 |
|  |  |  |  | 4 | 86 |  |  |  |  |
|  |  |  |  | 5 | 103 | 3.3 | 96.7 |  |  |
|  |  |  |  | 6 | 111 | 0.12 | 98.7 |  |  |

It will be appreciated that the instant specification and examples are set forth by way of illustration and not limitation, and that various modifications and changes may be made without departing from the spirit and scope of the present invention.

What is claimed is:

1. In the production of hydrazine wherein aqueous ammonia is oxidized in the presence of a ketone to form an aqueous solution containing at least one of a hydrazone and a ketazine along with ammonia, the hydrazone and ketazine are concentrated and the hydrazone and ketazine are subsequently hydrolyzed to 12. A process as claimed in claim 10, wherein the higher alcohol is a $C_7$-$C_9$ cut obtained from oxo synthesis.

13. A process as claimed in claim 1, wherein extraction is carried out with a molar ratio of ketone to total hydrazine of about 1 to 10.

14. A process as claimed in claim 1, wherein the volume ratio of the aqueous phase to the extractant phase is greater than about 1.

15. A process as claimed in claim 1, wherein unreacted ammonia is removed from the water-immiscible higher alcohol extract under a pressure of about 0.1 to 10 atmospheres.

16. A process as claimed in claim 1, wherein the hydrazone and ketazine are separated off from the water-immiscible higher alcohol extract by re-extraction with water.

17. A process as claimed in claim 16, wherein re-extraction is carried out with water containing free hydrazine at a molar ratio of total hydrazine in the extract : $N_2H_4$ in the water added of about 0.5 to 4.

18. A process as claimed in claim 1, wherein the hydrazone and ketazine present in the extract are hydrolyzed by the addition of water to form hydrazine and hydrazone, ketone being simultaneously distilled off, after which the free hydrazine and hydrazone are separated from the water-immiscible higher alcohol by re-extraction with water or by distillation.

19. A process as claimed in claim 18, wherein the molar ratio of water to total hydrazine during hydrolysis is between about 1 and 10.

20. A process as claimed in claim 1, wherein to the extract there is added an aqueous solution of an organic or inorganic acid thereby to form a ketone and hydrazinium salt.

21. A process as claimed in claim 20, wherein the acid is at least one member selected from the group consisting of HCl, HBr, $H_2SO_4$, acetic acid and oxalic acid.

22. A process as claimed in claim 1, wherein the extract is separated by distillation into an aqueous component containing hydrazine, ketazine and ketone, and into the water-immiscible solvent.

23. A process as claimed in claim 22, wherein distillation is carried out under a pressure of about 1 to 760 mm Hg.

24. In the production of hydrazine wherein aqueous ammonia is oxidized in the presence of a ketone to form an aqueous solution containing at least one of a hydrazone and a ketazine along with ammonia, the hydrazone and ketazine are concentrated and the hydrazone and ketazone are subsequently hydrolyzed to hydrazine and ketone, the improvement which comprises effecting the concentration of the hydrazone and ketazine by extracting the aqueous solution with a member selected from the group consisting of 2-chloraniline and 3-chloraniline whereby the hydrazone and ketazine preferentially enter the chloraniline, and separating the chloraniline extract from the aqueous solution.

* * * * *

UNITED STATES PATENT AND TRADEMARK OFFICE
CERTIFICATE OF CORRECTION

PATENT NO. : 4,005,179
DATED : January 25, 1977
INVENTOR(S) : Kurt-Wilhelm Eichenhofer et al It is certified that error appears in the above-identified patent and that said Letters Patent are hereby corrected as shown below:

Col. 1, line 44, cancel "in" and substitute -- is --.

Col. 9, line 14, after "hydrazine of" insert -- $\geq$ --.

Col. 13, line 43, after "ketazine" insert -- $\leq$ --.

Col. 17, Table 1(d), line 38, after "acetamide" insert -- $\cong$ --.

Signed and Sealed this

Eighteenth Day of July 1978

[SEAL]

Attest:

RUTH C. MASON
Attesting Officer

DONALD W. BANNER
Commissioner of Patents and Trademarks